United States Patent
Moffitt et al.

(10) Patent No.: US 7,499,748 B2
(45) Date of Patent: Mar. 3, 2009

(54) TRANSVASCULAR NEURAL STIMULATION DEVICE

(75) Inventors: Julia Moffitt, North Liberty, IA (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 373 days.

(21) Appl. No.: 11/103,245

(22) Filed: Apr. 11, 2005

(65) Prior Publication Data

US 2006/0229677 A1    Oct. 12, 2006

(51) Int. Cl.
  *A61N 1/36*    (2006.01)
(52) U.S. Cl. .......................... 607/9; 607/116
(58) Field of Classification Search .................. None
  See application file for complete search history.

(56) References Cited

U.S. PATENT DOCUMENTS

| | | | |
|---|---|---|---|
| 4,217,910 | A | 8/1980 | Khalil |
| 5,324,316 | A | 6/1994 | Schulman et al. |
| 5,354,318 | A | 10/1994 | Taepke |
| 5,501,703 | A | 3/1996 | Holsheimer et al. |
| 5,522,854 | A | 6/1996 | Ideker et al. |
| 5,531,779 | A | 7/1996 | Dahl et al. |
| 5,540,730 | A | 7/1996 | Terry, Jr. et al. |
| 6,006,134 | A | 12/1999 | Hill et al. |
| 6,141,588 | A | 10/2000 | Cox et al. |
| 6,164,284 | A | 12/2000 | Schulman et al. |
| 6,205,361 | B1 | 3/2001 | Kuzma et al. |
| 6,240,316 | B1 | 5/2001 | Richmond et al. |
| 6,292,695 | B1 | 9/2001 | Webster, Jr. et al. |
| 6,445,953 | B1 | 9/2002 | Bulkes et al. |
| 6,456,866 | B1 | 9/2002 | Tyler et al. |
| 6,522,926 | B1 * | 2/2003 | Kieval et al. .................. 607/44 |

(Continued)

FOREIGN PATENT DOCUMENTS

EP    1304135 A2    4/2003

(Continued)

OTHER PUBLICATIONS

Caparso, Anthony, et al., "System for Selective Activation of a Nerve Trunk Using a Transvascular Reshaping Lead", U.S. Appl. No. 11/130,022, filed May 16, 2005, 33 Pgs.

(Continued)

*Primary Examiner*—Kennedy J Schaetzle
(74) *Attorney, Agent, or Firm*—Schwegman, Lundberg & Woessner, P.A.

(57) ABSTRACT

This document discusses, among other things, apparatus, systems, and methods for transvascularly stimulation of a nerve or nerve trunk. In an example, an apparatus is configured to transvascularly stimulate a nerve trunk through a blood vessel. The apparatus includes an expandable electrode that is chronically implantable in a blood vessel proximate a nerve trunk. The expandable electrode is configured to abut a predetermined surface area of the vessel wall along a predetermined length of the vessel. An electrical lead is coupled to the expandable electrode. An implantable pulse generator is coupled to the lead and configured to deliver an electrical stimulation signal to the electrode through the lead. In an example method, an electrical signal is delivered from an implanted medical device to an electrode chronically implanted in a blood vessel proximate a nerve trunk to transvascularly deliver neural stimulation from the electrode to the nerve trunk.

28 Claims, 12 Drawing Sheets

U.S. PATENT DOCUMENTS

| | | | |
|---|---|---|---|
| 6,564,096 B2 | 5/2003 | Mest | |
| 6,584,362 B1 | 6/2003 | Scheiner et al. | |
| 6,656,960 B2 | 12/2003 | Puskas | |
| 6,778,854 B2 | 8/2004 | Puskas | |
| 6,804,561 B2 | 10/2004 | Stover | |
| RE38,705 E | 2/2005 | Hill et al. | |
| 6,934,583 B2 * | 8/2005 | Weinberg et al. | 607/9 |
| 2002/0026221 A1 | 2/2002 | Hill et al. | |
| 2002/0042637 A1 | 4/2002 | Stover | |
| 2002/0107557 A1 | 8/2002 | Edell et al. | |
| 2002/0161410 A1 | 10/2002 | Kramer et al. | |
| 2002/0183237 A1 | 12/2002 | Puskas | |
| 2002/0198570 A1 | 12/2002 | Puskas | |
| 2002/0198571 A1 | 12/2002 | Puskas | |
| 2003/0074039 A1 | 4/2003 | Puskas | |
| 2003/0114905 A1 | 6/2003 | Kuzma | |
| 2003/0158584 A1 | 8/2003 | Cates et al. | |
| 2003/0195578 A1 | 10/2003 | Perron et al. | |
| 2003/0199958 A1 | 10/2003 | Zhang et al. | |
| 2004/0030362 A1 | 2/2004 | Hill et al. | |
| 2004/0059383 A1 | 3/2004 | Puskas | |
| 2004/0186531 A1 | 9/2004 | Jahns et al. | |
| 2005/0065553 A1 | 3/2005 | Omry et al. | |
| 2005/0085864 A1 | 4/2005 | Schulman et al. | |
| 2005/0143412 A1 | 6/2005 | Puskas | |
| 2005/0143787 A1 | 6/2005 | Boveja et al. | |
| 2005/0187584 A1 | 8/2005 | Denker et al. | |
| 2005/0197675 A1 | 9/2005 | David et al. | |
| 2006/0079945 A1 | 4/2006 | Libbus | |
| 2006/0259107 A1 | 11/2006 | Caparso et al. | |
| 2007/0093875 A1 | 4/2007 | Chavan et al. | |

FOREIGN PATENT DOCUMENTS

| | | |
|---|---|---|
| WO | WO-9407564 A2 | 4/1994 |
| WO | WO-9965561 A1 | 12/1999 |
| WO | WO-03076008 A1 | 9/2003 |
| WO | WO-20060110338 A1 | 10/2006 |

OTHER PUBLICATIONS

Dunlap, M. E., et al., "Mechanisms of altered vagal control in heart failure: influence of muscarinic receptors and acetylcholinesterase activity", *Am J Physiol Heart Circ Physiol.*, 285(4), (Oct. 2003), H1632-40.

Grassi, G., et al., "Sympathetic response to ventricular extrasystolic beats in hypertension and heart failure", *Hypertension*, 39(4), (Apr. 2002), 886-91.

Leventhal, D. K., et al., "Subfascicle stimulation selectivity with the flat interface nerve electrode", *Annals of Biomedical Engineering*, 31(6), (Jun. 2003), 643-52.

Li, Meihua, "Vagal nerve stimulation markedly improves long-term survival after chronic heart failure in rats", *Circulation*, 109(1), Epub Dec. 8, 2003, (Jan. 6, 2004), 1-5.

Nolan, James, et al., "Prospective study of heart rate variability and mortality in chronic heart failure: results of the United Kingdom heart failure evaluation and assessment of risk trial (UK-heart).", *Circulation*, 98(15), (Oct. 13, 1998), 1510-1516.

Schauerte, P., "Catheter stimulation of cardiac parasympathetic nerves in humans: a novel approach to the cardiac autonomic nervous system", *Circulation*, 104(20), (Nov. 13, 2001), 2430-5.

Schauerte, Patrick N., et al., "Transvenous parasympathetic cardiac nerve stimulation: an approach for stable sinus rate control", *Journal of Cardiovascular Electrophysiology*, 10(11), (Nov. 1999), 1517-24.

Schauerte, Patrick N., et al., "Transvenous Parasympathetic Nerve Stimulation in the Inferior Vena Cava and Atrioventricular Conduction", *Journal of Cardiovascular Electrophysiology*, 11(1), (Jan. 2000), 64-69.

Sigurdsson, Axel, et al., "The role of neurohormonal activation in chronic heart failure and postmyocardial infarction", *American Heart Journal*, 132 (1 Pt 2 Su), (Jul. 1996), 229-234.

Thompson, Gregory W., et al., "Bradycardia induced by intravascular versus direct stimulation of the vagus nerve", *Annals of Thoracic Surgery*, 65(3), (Mar. 1998), 637-42.

Tyler, D. J., et al., "Chronic response of the rat sciatic nerve to the flat interface nerve electrode", *Annals of Biomedical Engineering*, 31(6), (Jun. 2003), 633-42.

Vanoli, Emilio, et al., "Vagal stimulation and prevention of sudden death in conscious dogs with a healed myocardial infarction", *Circulation Research*, 68(5), (May 1991), 1471-81.

"International Search Report and Written Opinion for Application No. PCT/US2006/011882, date mailed Aug. 2, 2006", 13 pages.

Jacobsson, F., et al., "The effect of transcutaneous electric nerve stimulation in patients with therapy-resistant hypertension", *J Hum Hypertens.*, 14(12), (Dec. 2000), 795-8.

"U.S. Appl. No. 11/130,022, Non-Final Office Action mailed May 15, 2008", 10 pgs.

"U.S. Appl. No. 11/256,907 Restriction Requirement mailed Mar. 21, 2008", 11 pgs.

"Structural Remodeling of Cardiac Myocytes in Hypertrophy and Progression to Failure; and, On Atrial Remodeling and Drug Treatment of Atrial Fibrillation", *In Cardia Remodeling and Failure, in Section II. Remodeling and Heart Failure*, Singal, et al., editors; Kluwer Academic Publishers, (2003), 183-93; 319-30.

* cited by examiner

TRANSVASCULAR NEURAL STIMULATION DEVICE

TECHNICAL FIELD

This patent document pertains generally to neural stimulation devices and methods, and more particularly, but not by way of limitation, to transvascular neural stimulation devices and methods.

BACKGROUND

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Some target areas can be difficult to stimulate or isolate. For example, it may be difficult to stimulate a nerve that is located deep in the body or behind an organ. Improved neural stimulation devices are needed.

SUMMARY

Various aspects of the present subject matter relate to an implantable apparatus. In an example, an apparatus is configured to transvascularly stimulate a nerve trunk through a blood vessel. The apparatus includes an expandable electrode that is chronically implantable in a blood vessel proximate a nerve trunk. The expandable electrode is configured to abut an area of the vessel wall along a length of the vessel. An electrical lead is coupled to the expandable electrode. An implantable pulse generator is coupled to the lead and configured to deliver an electrical stimulation signal to the electrode through the lead.

Various aspects of the present subject matter relate to a method. In an example method, an electrical signal is delivered from an implanted medical device to an electrode chronically implanted in a blood vessel proximate a nerve trunk to transvascularly deliver neural stimulation from the electrode to the nerve trunk.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. Additionally, the identified embodiments are not necessarily exclusive of each other, as some embodiments may be able to be combined with other embodiments. The following detailed description is, therefore, not to be taken in a limiting sense, and the scope is defined only by the appended claims, along with the full scope of legal equivalents to which such claims are entitled.

Overview

Figure 1A:
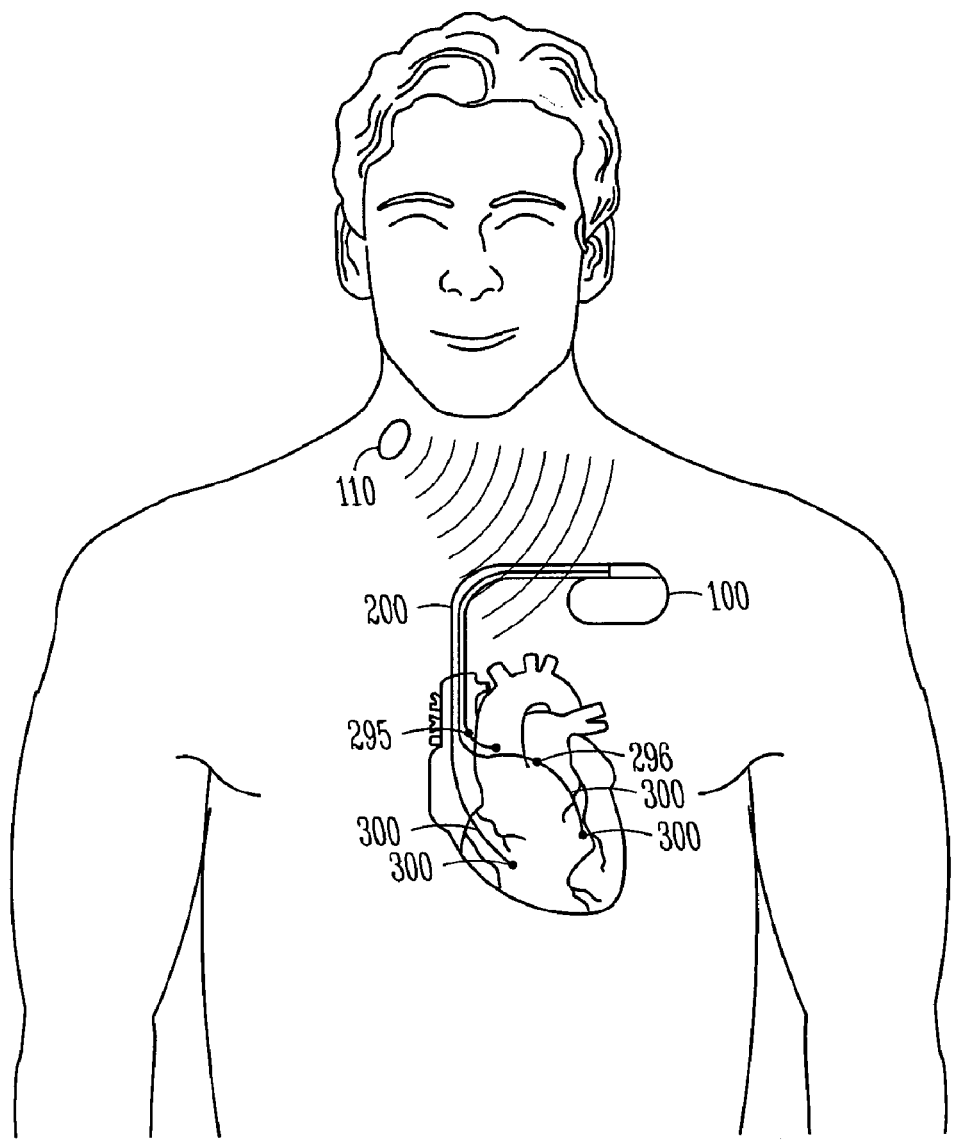
FIG. 1A shows a medical device implanted in a patient and leads extending into a heart, according to embodiments of the present subject matter.

Referring now to FIG. 1A, an embodiment of an implantable cardiac device 100 is placed subcutaneously or submuscularly in a patient's chest with leads 200 extending toward the heart. At least one lead 200 is coupled to an electrode 295 that is placed in a blood vessel and positioned to transvascularly stimulate a nerve on or near the extravascular surface of the vessel. Transvascular stimulation avoids direct contact with nerves during stimulation and reduces problems associated with neural inflammation or injury induced by direct stimulation. Leads can be implanted through the vasculature, thus maintaining the integrity of the thorax. Transvascular stimulation using intravascularly-fed leads provides relatively non-invasive access to anatomical targets and points of innervation in comparison to cuff electrodes.

Figure 1B:
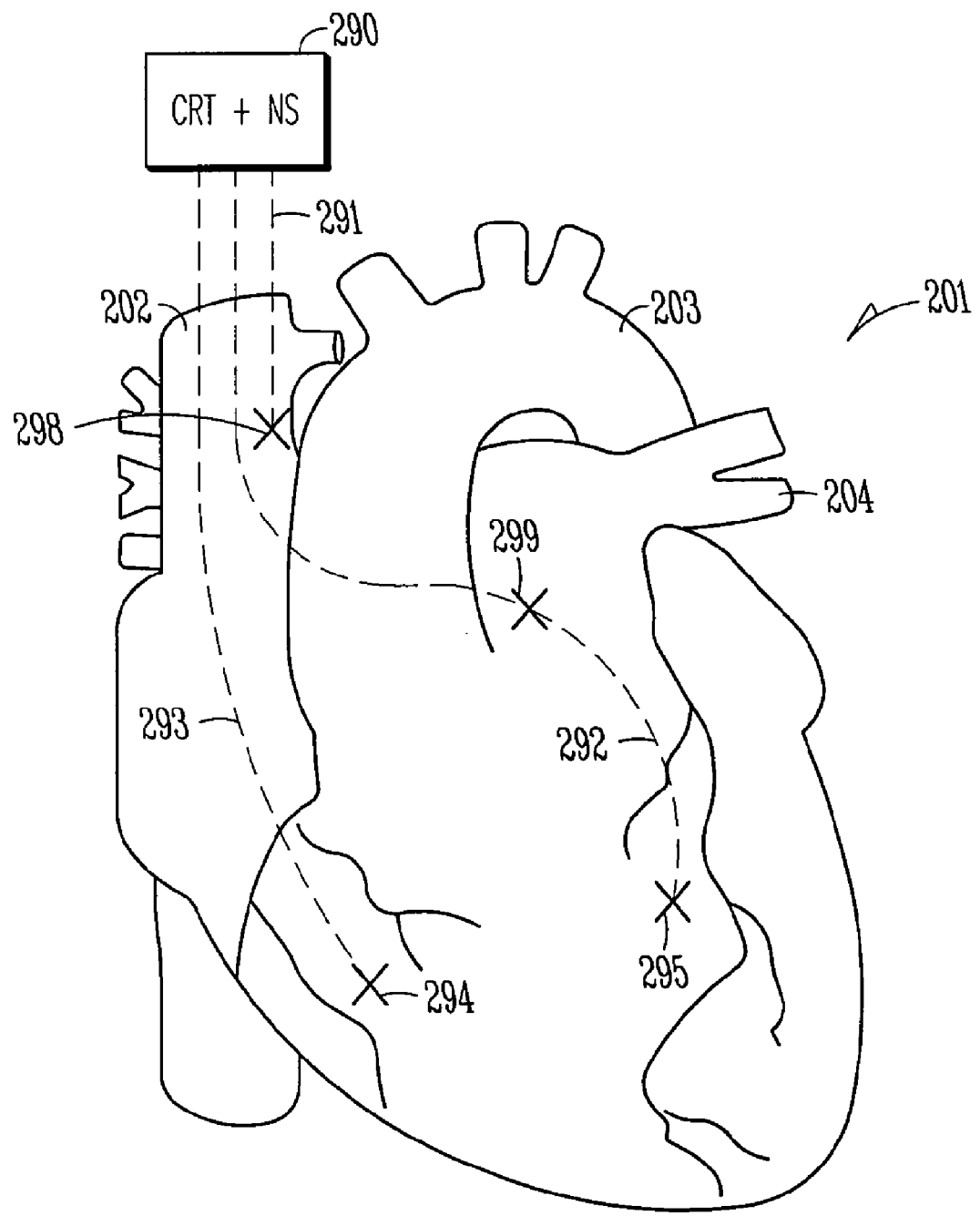
FIG. 1B is an illustration of a heart and leads extending into the heart, according to embodiments of the present subject matter.
Figure 1C:
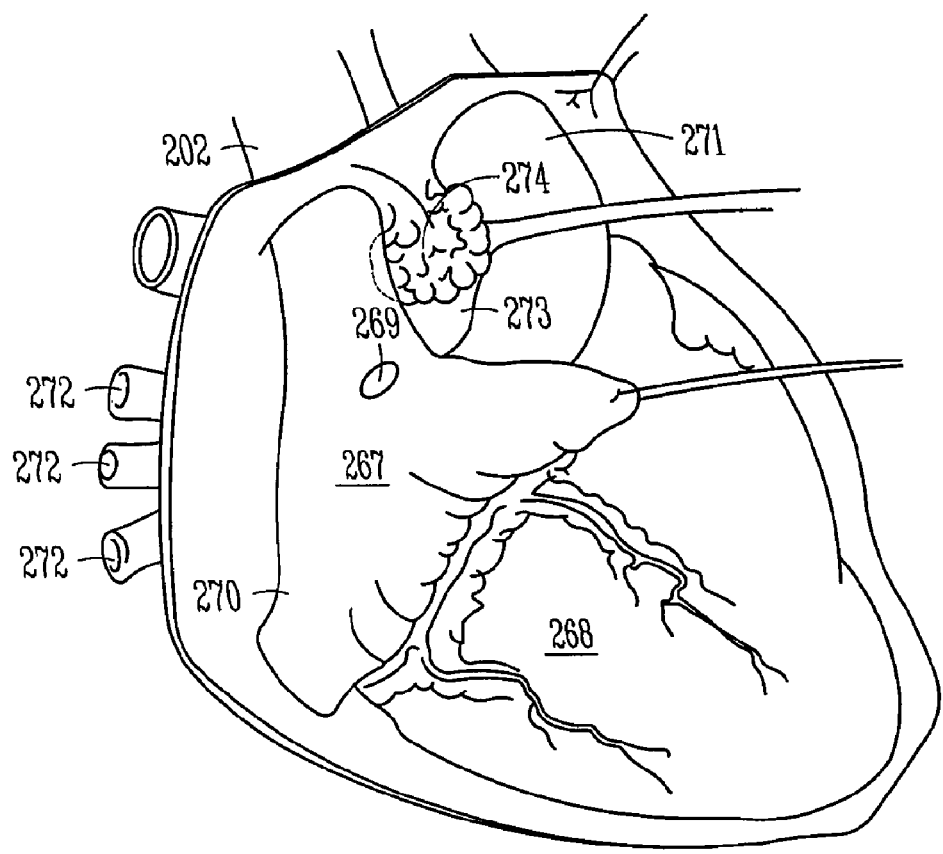
FIGS. 1C and 1D are illustrations of a heart and related blood vessels.
Figure 1D:
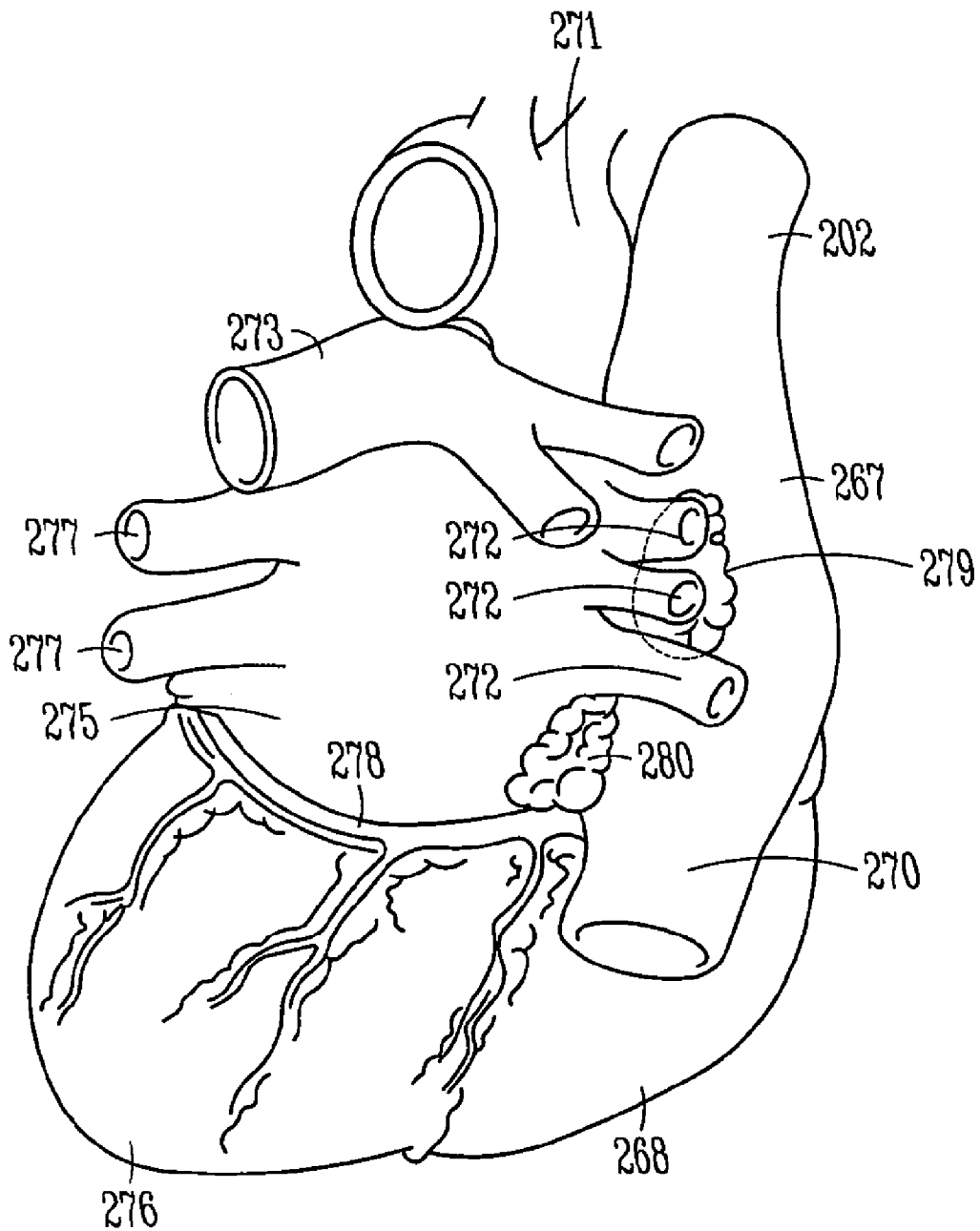
Figure 1E:
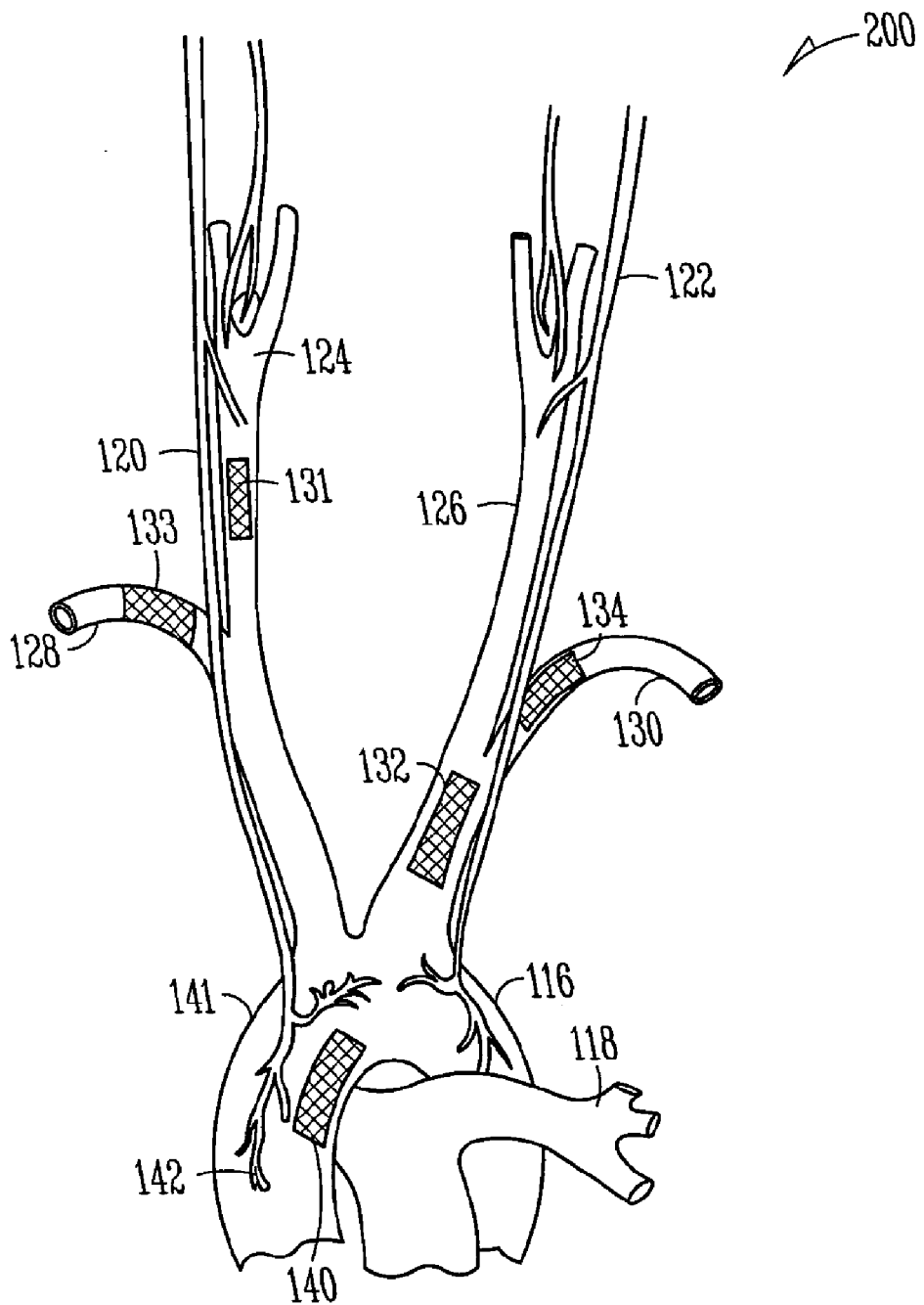
FIG. 1E is an illustration of blood vessels and nerve trunks.
Figure 2A:
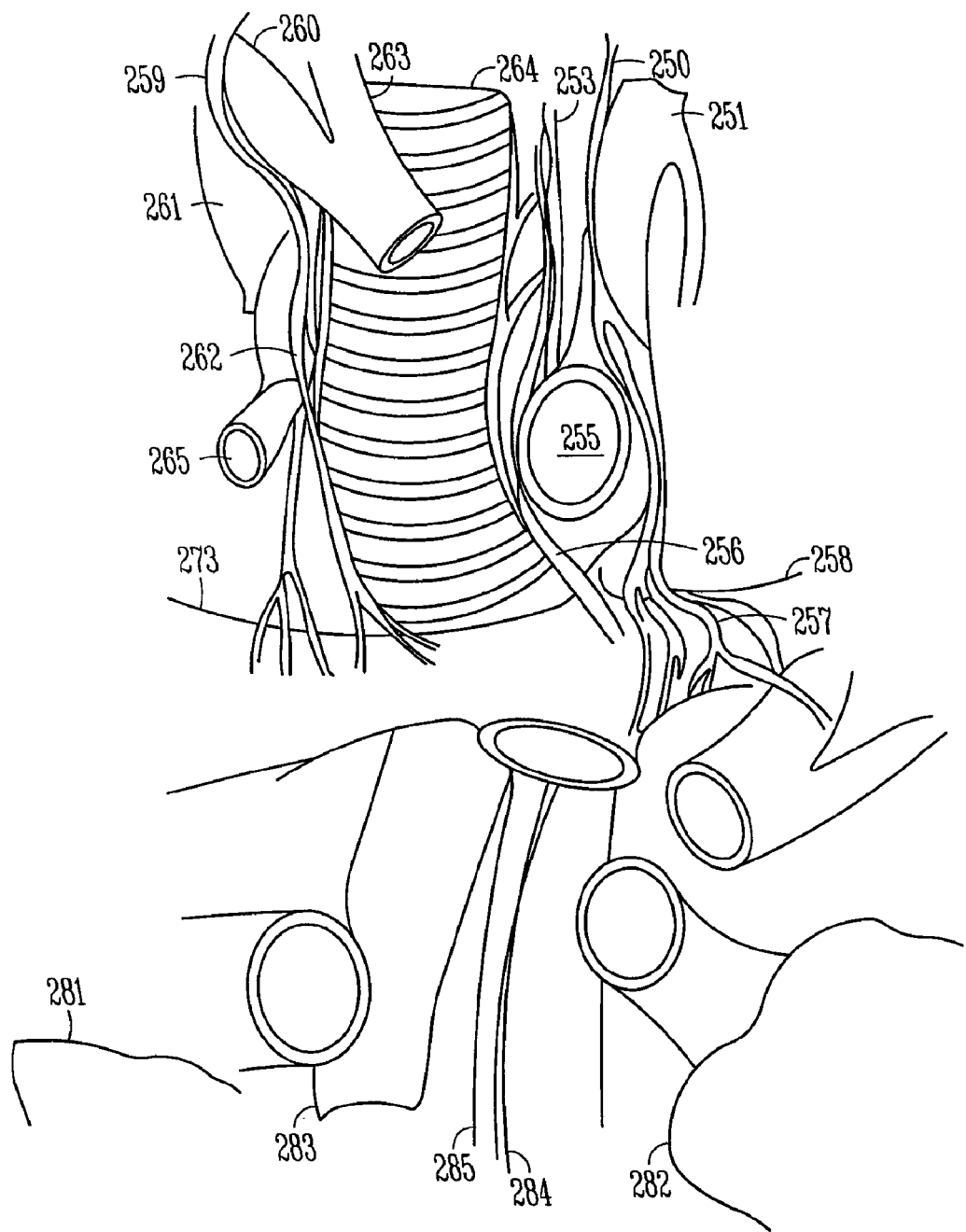
FIGS. 2A and 2B are illustrations of stimulation targets.
Figure 2B:
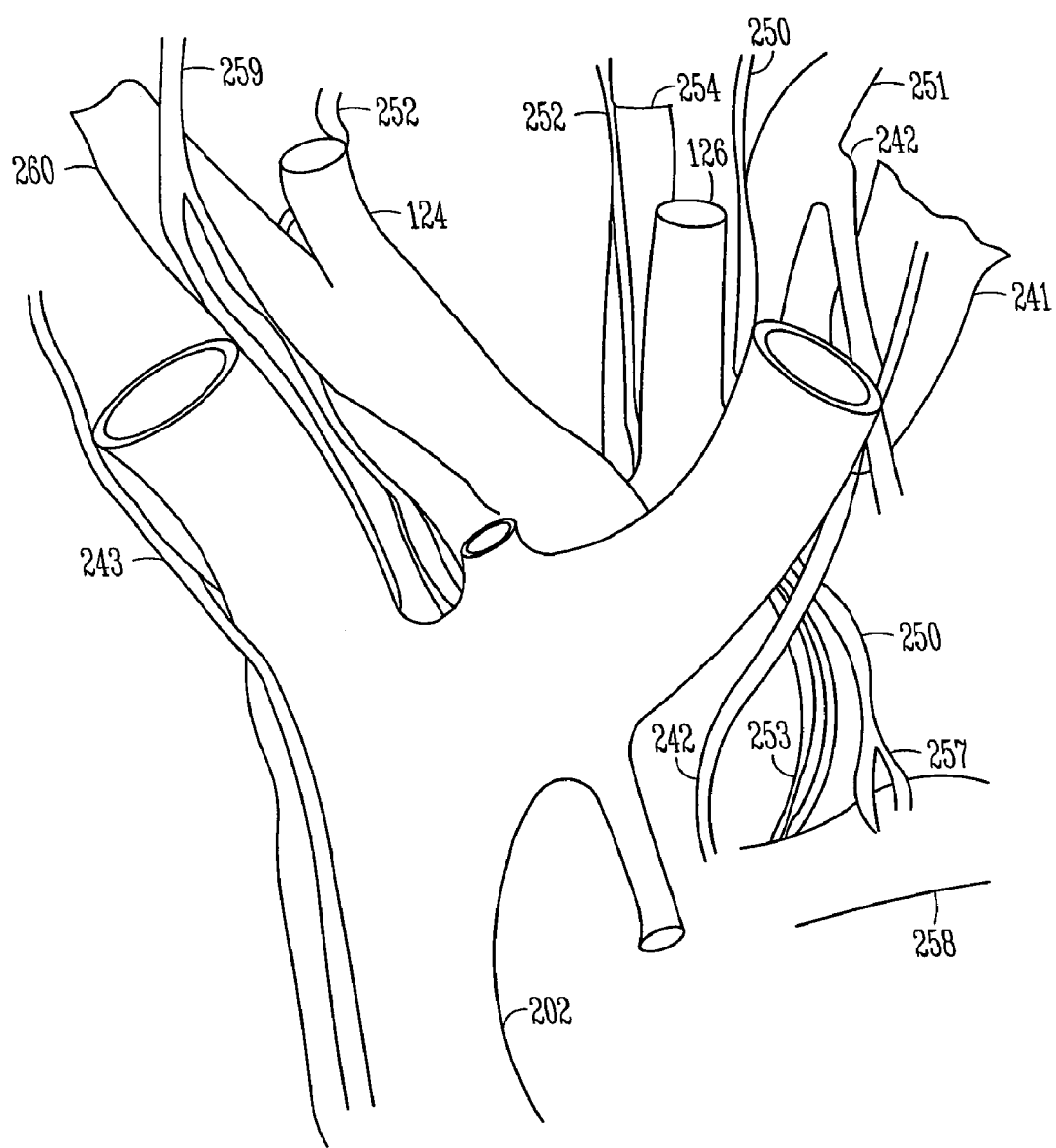
Figure 2C:
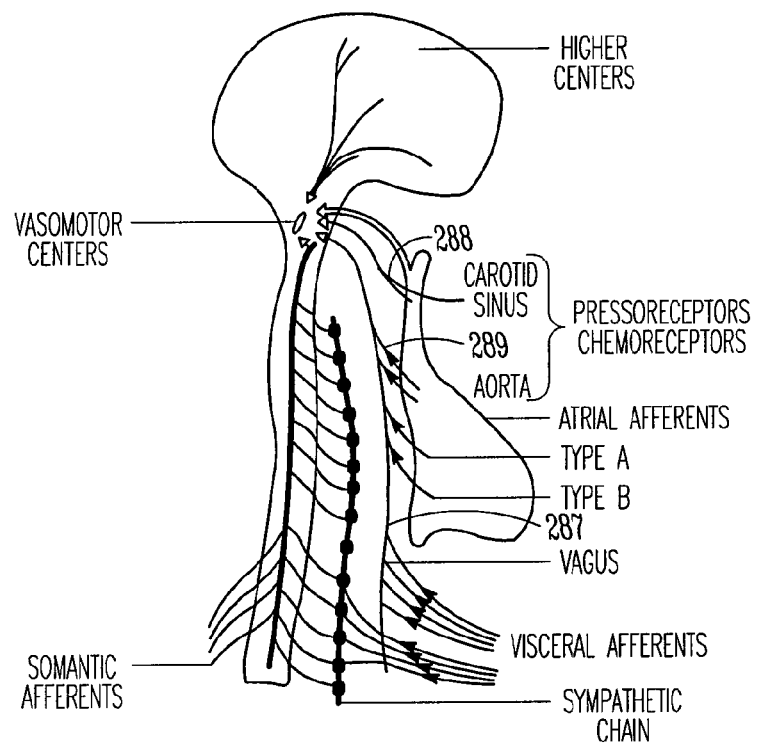
FIGS. 2C and 2D show neural pathways.
Figure 3A:
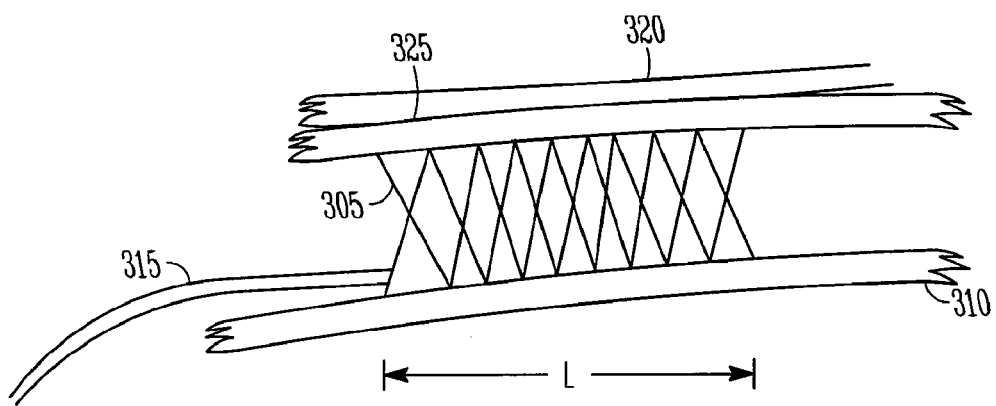
FIGS. 3A and 3B are illustrations of expandable electrodes chronically implanted in a blood vessel.
Figure 3B:
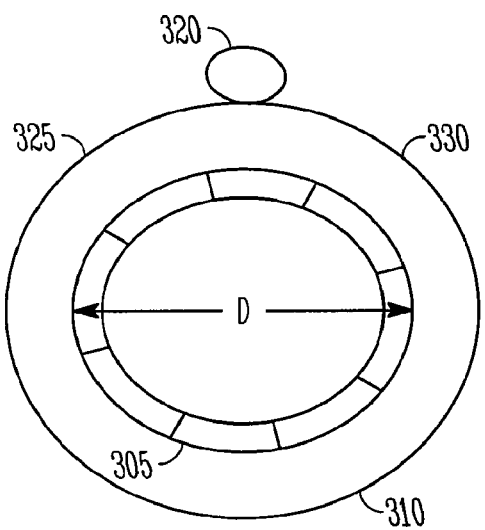
Figure 4:
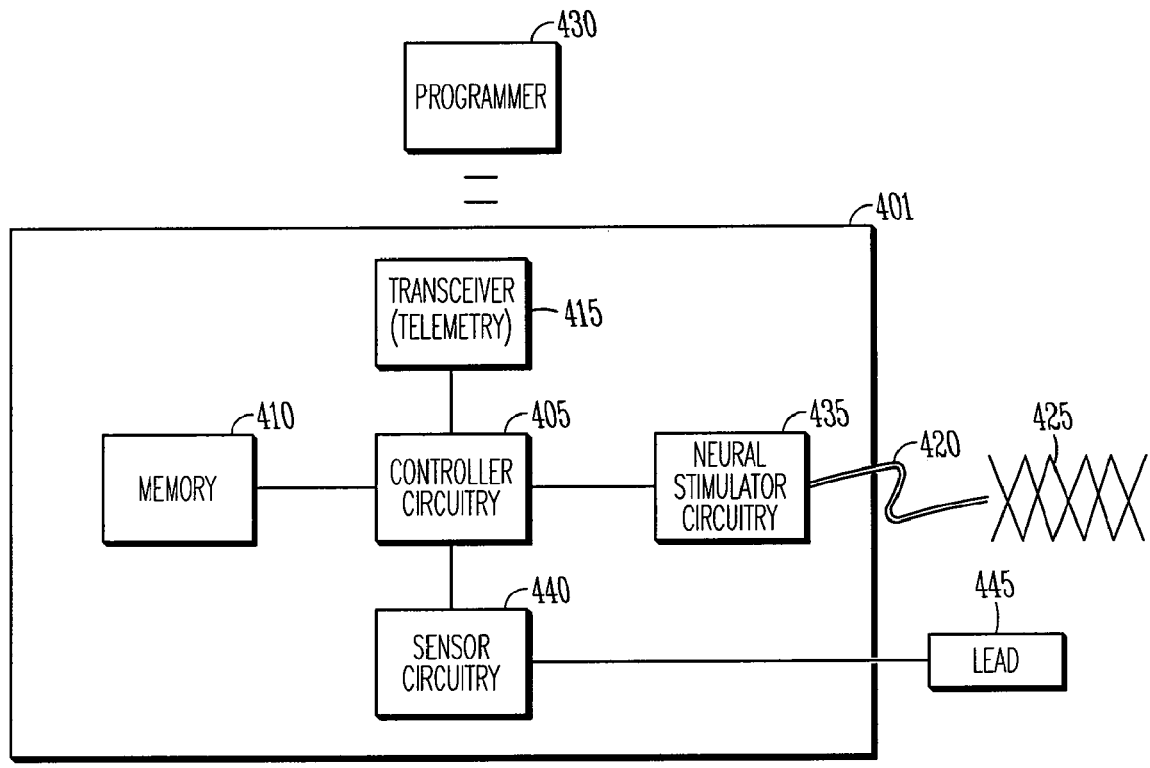
FIG. 4 is a schematic illustration of an implantable system for delivering transvascular stimulation.
Figure 5:
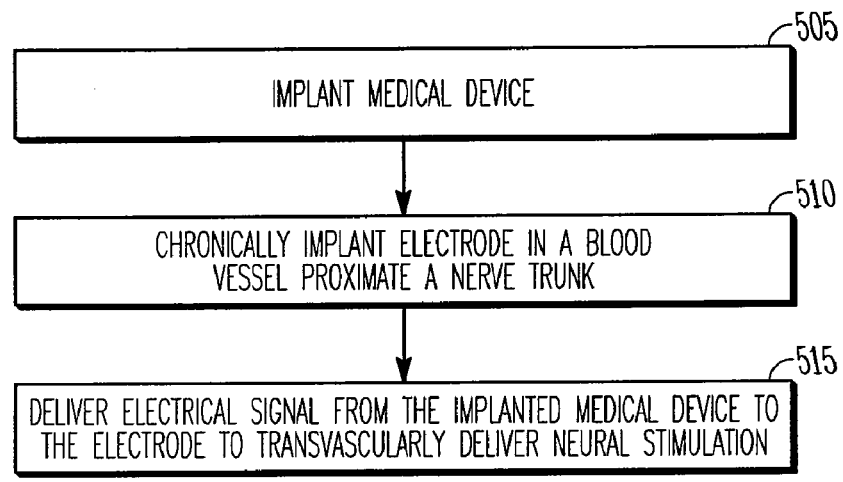
FIGS. 5 and 6 are flowcharts that illustrate methods of delivering transvascular stimulation.
Figure 6:
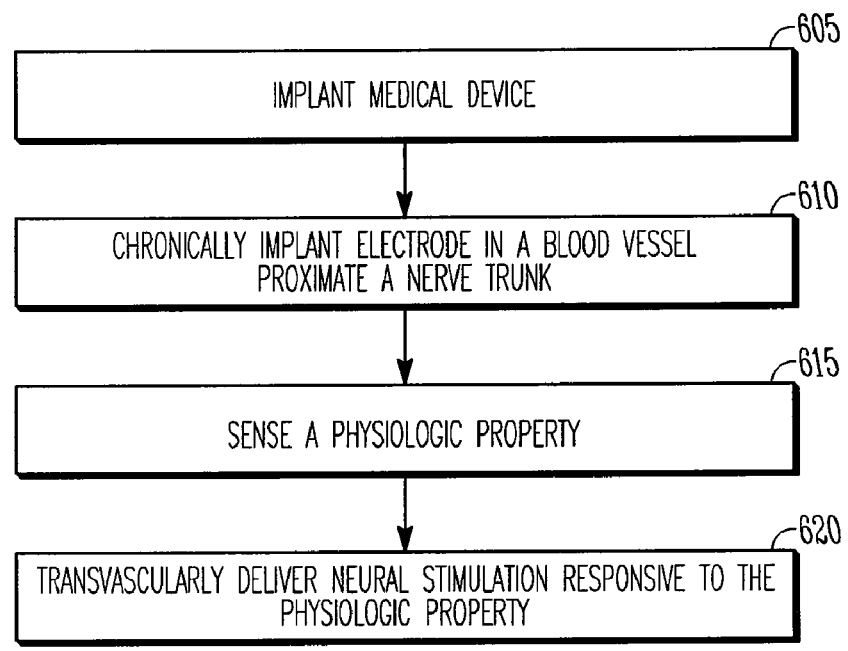

FIGS. 1B-1E and FIGS. 2A-2B illustrate examples of electrode placement. FIGS. 2B-2C show neural pathways. FIGS. 3A-3B show an example an electrode implanted in a blood vessel. FIG. 4 shows a schematic representation of an example of an implantable system for delivering transvascular stimulation. FIGS. 5 and 6 are flow charts that illustrate methods of delivering transvascular stimulation.

Electrode Examples

FIG. 3A is shows a cross-section of an example expandable electrode 305 implanted in a blood vessel 310. In an example, the expandable electrode includes a mesh, at least part of which is electrically conductive. In an example, the expandable electrode is formed from Platinum or Platinum-Iridium. In an embodiment, the expandable electrode 305 is similar to a stent.

Referring again to FIG. 3A, a nerve trunk 320 extends on or near an extravascular surface 325 of the blood vessel 310. An expandable electrode 305 is implanted at or near a location in the blood vessel where the nerve trunk 320 crosses the blood vessel. In an example, the expandable electrode transmits neural stimulation energy through a predetermined surface area of the wall of a blood vessel. In an example, this predetermined area is about 0.25 to 5 cm$^2$. In an example, the expandable electrode has a length L that provides enough surface area that there is at least some flexibility in the placement of the expandable electrode in the vessel with respect to the target nerve. In an example, the length of the expandable electrode is about 0.5 to 2.0 cm.

In an example, the entire surface area of the expandable electrode that touches the blood vessel wall is conductive. In an alternative example, at least a part of the surface area of the electrode is non-conductive. For example, an electrode can be formed and positioned to deliver stimulation to through a conductive part of the electrode to a portion 330 (FIG. 3B) of a blood vessel that is proximate a nerve.

FIG. 3B shows an end view of the blood vessel and electrode of FIG. 3A. The expandable electrode has an expanded diameter D (shown in FIG. 3B) that is sized for implantation in a blood vessel of a particular size range. In one example, where the electrode is size for implantation in the internal jugular vein, the expanded diameter D is about 0.5 to 1.5 cm, and the length L of the electrode is about 1.0 cm.

In an example, the expandable electrode is covered with a drug, such as a drug that prevents occlusion, or a drug that reduces inflammation of the blood vessel near the electrode.

The expandable electrode 305 is coupled to a power source that delivers an electrical stimulation. In FIG. 3A, the illustrated expandable electrode 305 is coupled to a lead 315. The lead 315 is coupled to an implantable system or device that includes control circuitry, such as the device shown in FIG. 1 or the system shown in FIG. 4.

Electrode Placement and Nerve Targets

The electrode may be implanted in various locations in the body, including a variety of locations near a trunk or branch of a sympathetic or parasympathetic nerve system.

Referring again to the example shown in FIG. 1A, the location of implanted electrodes 295, 296 is denoted by an X. The implanted electrodes 295, 296 each transvascularly stimulate a sympathetic nerve or a parasympathetic nerve. In an example, the electrode 295 transvascularly stimulates a peripheral nerve trunk. Examples of a peripheral nerve trunk include the vagus nerve 287, aortic nerve 288, and carotid sinus nerve 289, which are shown in FIG. 2C. In another example, the electrode 295 stimulates a nerve branch, such as a vagal cardiac branch.

FIGS. 1B, 1C, and 1D show examples of blood vessels in which the electrode can be implanted. FIG. 1B shows an implantable device 290, leads 291, 292, 293 extending into a heart 201 and a superior vena cava 202, an aortic arch 203, and a pulmonary artery 204. Leads extending into the heart are shown as dotted lines. For simplicity, electrodes are denoted with an X. Lead 291 and electrode 298 are inserted in the superior vena cava (SVC) 202. The electrode 298 is used to transvascularly stimulate a nerve or nerve trunk on or near the SVC 202. CRM lead 292 is intravascularly inserted through a peripheral vein into the coronary sinus and into the left ventricle. Electrode 299 is implanted in the coronary sinus and coupled to the CRM lead 292. FIG. 1B also shows electrodes 294 and 295, which are examples of sensing or pacing electrodes located in the right and left ventricles respectively. Physiological data sensed by one or both of the electrodes 294, 295 is processed by the device 290, and a responsive neurostimulation therapy is delivered by one or more of the electrodes 298, 299.

FIGS. 1C and 1D illustrate other bloods vessels on the right side and left side of the heart respectively in which an electrode is implantable. FIG. 1C shows the right atrium 267, right ventricle 268, sinoatrial node 269, superior vena cava 202, inferior vena cava 270, aorta 271, right pulmonary veins 272, and right pulmonary artery 273. FIG. 1D shows the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. An electrode can be implanted in one or more of the blood vessels listed above at a location where a nerve, nerve branch, or nerve trunk passes an extravascular surface of the blood vessel. The implanted electrode transvascularly stimulates a nerve, nerve branch, or nerve trunk through the blood vessel. In one example, an electrode is implanted in the SVC 202 near a nerve a vagal nerve trunk. In another example, an electrode is implanted in the coronary sinus 278 near a vagal nerve trunk.

In another example, a cardiac fat pad is transvascularly stimulated by an implanted electrode. FIG. 1C illustrates a cardiac fat pad 274 between the superior vena cava and aorta. FIG. 1D illustrates a cardiac fat pad 279 located proximate to the right cardiac veins and a cardiac fat pad 280 located proximate to the inferior vena cava and left atrium. An electrode implanted in the superior vena cava, aorta, cardiac veins, or inferior vena cava stimulates nerve endings in fat pad 274 or 279. Nerve endings in the fat pad 280 are stimulated by an electrode located in the coronary sinus.

Referring now to FIG. 1E, in an example, electrodes 131, 132, 133, 134 are implanted at locations in blood vessels near a vagus nerve. Portions of arteries are shown cut-away so that the electrodes are visible in the figure. The aortic arch 116, pulmonary artery 118, carotid arteries 124, 126 and subclavian arteries 128, 130 are shown in FIG. 1E. The right vagus nerve trunk 120 extends near carotid artery 124 and subclavian artery 128. The left vagus nerve 122 extends near carotid artery 126 and subclavian artery 130. Electrode 131 is implanted in carotid artery 124. The illustrated electrode 131 is an expandable electrode such as a stent. Electrode 132 is implanted in carotid artery 126. Electrode 133 is implanted in subclavian artery 128. Electrode 134 is implanted in subclavian artery 130. Electrode 140 is implanted in the carotid sinus 141 near the carotid sinus nerve 142. In an example, only one of electrodes 131, 132, 133, 134, 140 is implanted in a patient. In another example, two or more electrodes are implanted in a patient and used to transvascularly stimulate a nerve trunk.

FIGS. 2A and 2B provide additional illustrations of nerve target examples near the heart. FIG. 2A shows left vagus nerve 250 extending next to a subclavian artery 251. Various nerves extend around the arch of the aorta 255. Vagus nerve 250 also extends past the ligamentum arteriosum 256. The anterior pulmonary plexus 257 crosses the left pulmonary artery 258. Right vagus nerve 259 extends past a subclavian artery 260 and the cupola of pleura 261. Cardiac nerves 262 extend past the brachiocephalic trunk 263 near the trachea 264. Cardiac nerves 262 also extend past the arch of an azygos vein 265 to the right pulmonary artery 273. In the lower portion of FIG. 2A appear the right lung 281, left lung 282, esophagus 283, a lower portion 284 of the left vagus nerve 250, and a lower portion 285 of the aorta. FIG. 2B shows a left phrenic nerve 240 extending past a cupola of pleura 241, an internal thoracic artery 242, and left pulmonary artery 258 Vagus nerve 250, recurrent laryngeal nerves 252, cardiac nerves 253, and the anterior pulmonary plexus 257 extend near the left pulmonary artery 258 and ligamentum arteriosum. An expandable electrode, such as a stent, is chronically implantable in the blood vessels shown in FIG. 2A or 2B to transvascularly stimulate a nerve or nerve trunk that extends on or near the blood vessel. In one example, the vagus nerve is transvascularly stimulated from the azygos vein 265 or internal jugular vein.

Figure 2D:
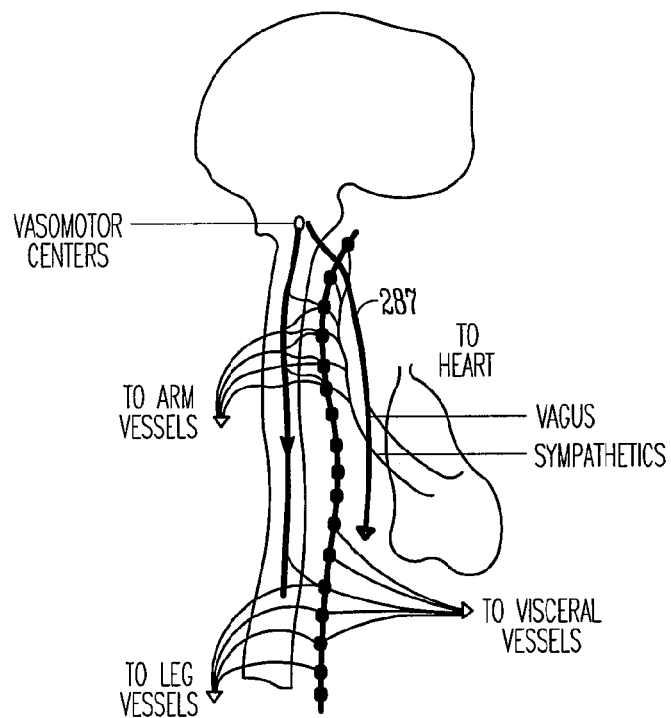

FIGS. 2C and 2D show nerve pathways. FIG. 2C generally illustrates afferent nerves to vasomotor centers. An afferent nerve conveys impulses toward a nerve center. A vasomotor center relates to nerves that dilate and constrict blood vessels to control the size of the blood vessels. FIG. 2D generally illustrates efferent nerves from vasomotor centers. An efferent nerve conveys impulses away from a nerve center. Afferent and efferent nerves can be stimulated transvascularly.

Figure 2E:
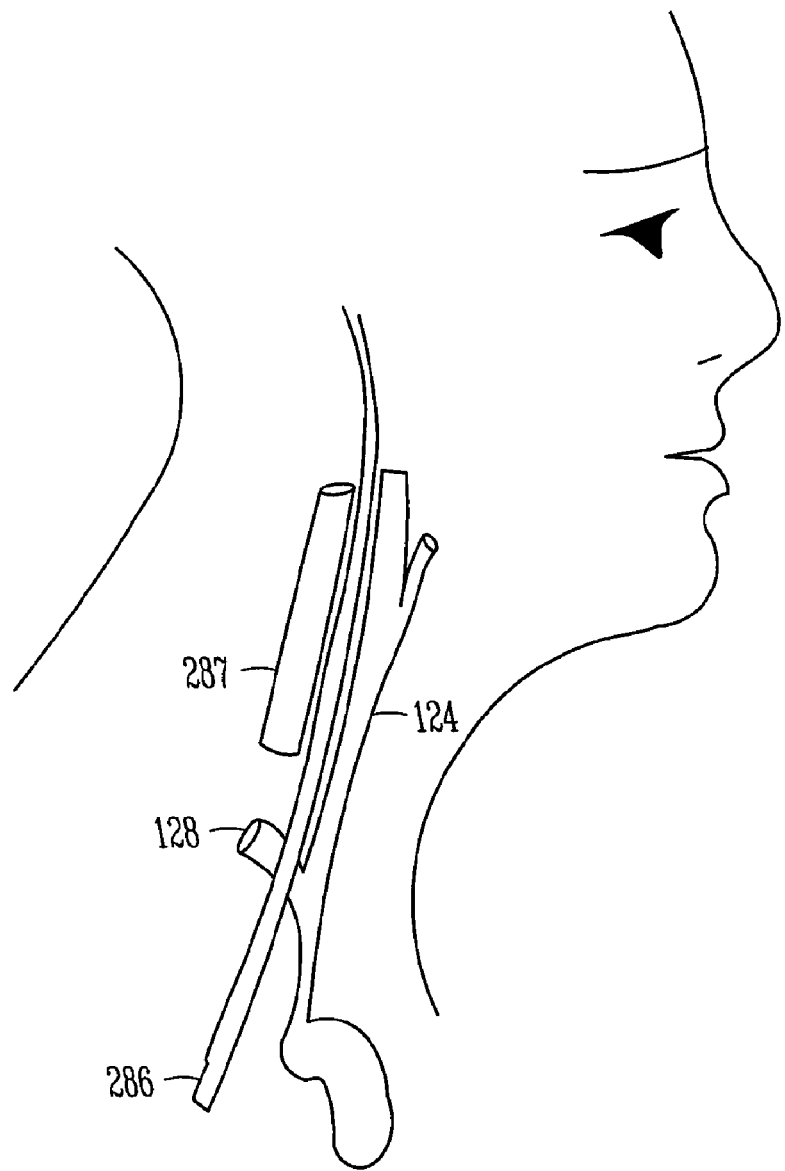
FIG. 2E is an illustration of an internal jugular vein near a vagus nerve.

FIG. 2E shows the vagus nerve 286 near the internal jugular vein 287. In an example, the vagus nerve 286 is transvascularly stimulated from the internal jugular vein 287. A common carotid artery 124 and subclavian artery 128 are also shown in FIG. 2E.

In other examples, nerve trunks innervating other organs, such as the lungs or kidneys are transvascularly stimulated. In an example, an expandable electrode such as a stent is implanted in a blood vessel proximate a nerve or nerve trunk that innervates the lungs or kidneys.

Device and System

Referring again to the example shown in FIG. 1A, an implantable device 100 is coupled to a lead 200 that is inserted into a blood vessel and coupled to an electrode 295. An electrical signal is delivered through the lead 200 to the electrode 295, which transvascularly stimulates a nerve on an extravascular surface of the blood vessel. The device 100 can optionally also deliver cardiac resynchronization therapy (CRT) through one or more CRT leads that are threaded intravenously into the heart. The CRT leads connect the device 100 to electrodes 300 that are used for sensing or pacing of the atria and/or ventricles. Transvascular stimulation electrode 296 is coupled to a CRT lead. Some embodiments process intrinsic electrical heart signals and deliver a responsive neural stimulation therapy through one of the electrodes 295, 296. An optional satellite unit 110 includes an electrode for neural stimulation and a communication circuit that communicates with the device 100 via a wireless link or conduction through the body. The satellite unit 110 electrode is implanted in a blood vessel, such as an internal jugular vein, to transvascularly stimulate a nerve, such as a vagus nerve, through the wall of the blood vessel.

FIG. 4 is a schematic illustration of an example transvascular stimulation system that includes an implantable device 401, an electrical lead 420 coupled to the implantable device 401, and an expandable stimulation electrode 425. The implantable device includes a controller circuit 405, a memory circuit 410, a telemetry circuit 415, and a neural stimulation circuit 435. The controller circuit 405 is operable on instructions stored in the memory circuit to deliver an electrical stimulation therapy. Therapy is delivered by the neural stimulation circuit 435 through the lead 420 and the electrode 425. The telemetry circuit 415 allows communication with an external programmer 430. The illustrated system also includes optional sensor circuitry 440 that is coupled to a lead 445. The controller circuit 405 processes sensor data from the sensor circuitry and delivers a therapy responsive to the sensor data.

Therapies

Neural stimulation therapies can be used to treat one or more of a variety of conditions, including but not limited to arrhythmias, heart failure, hypertension, syncope, or orthostatic intolerance. In an example, an efferent peripheral nerve is transvascularly stimulated by an implanted expandable electrode. In another example, an afferent peripheral nerve is stimulated.

In an example, electrical stimulation is transvascularly delivered to a parasympathetic nerve to reduce chronotropic, ionotropic, and dromotropic responses in the heart. In a therapy example, electrical stimulation is transvascularly delivered to a parasympathetic nerve trunk during heart failure. In another therapy example, electrical stimulation is transvascularly delivered to a parasympathetic nerve trunk following a myocardial infarction to protect against arrhythmias or prevent cardiac remodeling.

Transvascular stimulation of a vagus nerve trunk is used in a number of therapies. In an example, vagal nerve stimulation simultaneously increases parasympathetic tone and decreases sympathetic myocardial tone. In an example, a vagus nerve trunk is transvascularly stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, vagal stimulation from the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, transvascular neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by transvascularly stimulating a sympathetic nerve trunk. In another example, the ionotropic state of the heart is increased by transvascularly stimulating a sympathetic nerve trunk.

Methods for Delivering Transvascular Stimulation

Referring now to FIG. 5, an example method of delivering transvascular neural stimulation includes implanting a medical device, at 505. At 510, an electrode is chronically implanted in a blood vessel near a nerve trunk, such as a cardiac peripheral nerve trunk. In an example, the electrode is an expandable electrode, such as a stent. In an example, the expandable electrode has an expanded diameter that is dimensioned to fix the electrode in place by frictional forces. In an example, the expandable electrode includes a drug-eluting coating that prevents occlusion or prevents inflammation of vascular walls or nerves that receives electrical stimulation from the electrode. In an example, the electrode is implanted in a blood vessel at a location where the nerve trunk extends along an extravascular surface of the blood vessel. In an example, the electrode is implanted in a blood vessel near a peripheral nerve trunk. In an example, the peripheral nerve trunk includes a sympathetic or parasympathetic nerve. In an example, the electrode is implanted near a vagal cardiac nerve in a blood vessel such as the SVC, coronary sinus, or an azygos vein. In another example, the electrode is implanted in an internal jugular vein.

Returning to FIG. 5, at 515, an electrical signal is delivered from the implanted device to the electrode to transvascularly deliver neural stimulation to a nerve trunk near the blood vessel. In an example, the electrode delivers an electric pulse therapy that is sufficient to elicit depolarization of a target nerve. In an example, the stimulation therapy delivers about 1-10 milliamps of electrical stimulation. In an example, the controller delivers a pulse train of about 10-120 hertz to the electrode. In one example, a pulse train of about 20 hertz is used. In an example, delivery of transvascular neural stimulation near the heart is timed to occur during the cardiac refractory period to prevent fibrillation.

In an example, transvascularly stimulating a parasympathetic nerve inhibits cardiac remodeling or delivers an antiarrhythmia therapy following a myocardial infarction. In another example, transvascularly stimulating a sympathetic nerve delivers an antibradycardia therapy.

FIG. 6 is a flow chart that illustrates another method. A medical device is implanted at 605. At 610, an electrode is chronically implanted in a blood vessel near a nerve trunk. At 615, a physiologic property is sensed. In an example, an intrinsic electrical heart signal is detected. In another example, blood pressure is detected. At 620, neural stimulation responsive to the sensed physiologic property is transvascularly delivered through the implanted electrode.

What is claimed is:

1. An implantable apparatus for transvasculary stimulating a vagus nerve trunk in a cervical region from an internal jugular vein (IJV) to provide a therapy to inhibit heart failure remodeling, the apparatus comprising:
    an expandable electrode chronically implantable in the IJV, the expandable electrode configured to abut an intravascular surface of the IJV in the cervical region proximate the vagus nerve trunk;
    an electrical lead coupled to the expandable electrode, the electrical lead adapted to be intravascularly fed into the IJV;
    an implantable pulse generator coupled to the lead and configured to deliver an electrical stimulation signal to the electrode through the lead, wherein the apparatus is configured to transvascularly stimulate the vagus nerve trunk from the IJV; and
    a controller adapted to control the pulse generator to deliver a programmable electrical pulse therapy to inhibit heart failure remodeling, wherein the therapy to inhibit heart failure remodeling includes stimulating to the vagus nerve in the cervical region.

2. The apparatus of claim 1, wherein the expandable electrode is configured to abut a predetermined surface area of a wall of the IJV along a predetermined length of the IJV.

3. The apparatus of claim 2, wherein the predetermined length is about 1 centimeter.

4. The apparatus of claim 3, wherein the expandable electrode has an expanded diameter is about 0.5 to 1.5 cm.

5. The apparatus of claim 2, wherein the predetermined surface area is about 0.25 to 5 cm$^2$.

6. The apparatus of claim 5, wherein the expandable electrode has a length about 0.5 to 2.0 cm.

7. The system of claim 5, wherein the expandable electrode has a length about 0.5 to 2.0 cm, a predetermined surface area to touch a wall of the IJV of about 0.25 to 5 cm$^2$, and an expanded diameter of about 0.5 to 1.5 cm.

8. The system of claim 5, further comprising a right ventricle lead and a left ventricle lead, wherein the system is adapted to capture myocardial tissue using the right ventricle lead and the left ventricle lead, and the system is adapted to deliver cardiac resynchronization therapy using the left and right ventricle leads.

9. The system of claim 5, further comprising at least one of a right ventricle lead or a left ventricle lead, wherein the system is adapted to pace the right or left ventricle using the right ventricle lead or the left ventricle lead.

10. The apparatus of claim 1, wherein the expandable electrode includes a mesh, at least part of the mesh being conductive.

11. The apparatus of claim 10, wherein the expandable electrode has a surface area to touch a wall of the IJV, and all of the surface area is conductive.

12. The apparatus of claim 10, wherein the expandable electrode has a surface area to touch a wall of the IJV, and some of the surface area is non-conductive.

13. The apparatus of claim 1, wherein the expandable electrode includes a drug-eluting component that is configured to be implanted inside the IJV.

14. The apparatus of claim 13, wherein the drug-eluting component is adapted to elute a drug to prevent occlusion.

15. The apparatus of claim 13, wherein the drug-eluting component is adapted to elute a drug to reduce inflammation.

16. The apparatus of claim 1, wherein the expandable electrode included platinum or platinum-iridium.

17. The apparatus of claim 1, further comprising a right ventricle lead and a left ventricle lead, wherein the apparatus is adapted to capture myocardial tissue using the right ventricle lead and the left ventricle lead, and the apparatus is adapted to deliver cardiac resynchronization therapy using the left and right ventricle leads.

18. The apparatus of claim 1, further comprising at least one of a right ventricle lead or a left ventricle lead, wherein the apparatus is adapted to pace the right or left ventricle using the right ventricle lead or the left ventricle lead.

19. A system for transvasculary stimulating a vagus nerve trunk in a cervical region from an internal jugular vein (IJV) to provide a therapy to inhibit heart failure remodeling, the system comprising:
    an expandable electrode implantable in the IJV in the cervical region proximate the vagus nerve trunk;
    a lead assembly coupled to the expandable electrode, the lead assembly including an electrical lead adapted to be intravascularly fed into the IJV; and
    an implantable device coupled to the lead assembly, the implantable device including a controller circuit to communicate with a neural stimulator, a telemetry circuit to communicate with the controller circuit and an external module, a memory circuit to communicate with the controller circuit, and computer-readable instructions embedded in the memory circuit, the computer-readable instructions being operable on by the controller to deliver a programmable electric pulse therapy from the neural stimulator through the expandable electrode to the vagus nerve trunk to inhibit cardiac remodeling from heart failure.

20. The system of claim 19, wherein the expandable electrode includes a stent.

21. The system of claim 19, wherein the expandable electrode has a length about 0.5 to 2.0 cm, a predetermined surface area to touch a wall of the IJV of about 0.25 to 5 cm$^2$, and an expanded diameter of about 0.5 to 1.5 cm.

22. The system of claim 19, further comprising a right ventricle lead and a left ventricle lead, wherein the system is adapted to capture myocardial tissue using the right ventricle lead and the left ventricle lead, and the system is adapted to deliver cardiac resynchronization therapy using the left and right ventricle leads.

23. The system of claim 19, further comprising at least one of a right ventricle lead or a left ventricle lead, wherein the system is adapted to pace the right or left ventricle using the right ventricle lead or the left ventricle lead.

24. A system for transvasculary stimulating a vagus nerve trunk in a cervical region from an internal jugular vein (IJV) in a cervical region to provide a therapy to inhibit heart failure remodeling, the system comprising:
an expandable electrode implantable in the IJV within the cervical region proximate the vagus nerve trunk;
a lead assembly coupled to the expandable electrode, the lead assembly including an electrical lead adapted to be intravascularly fed into the IJV; and
an implantable device coupled to the lead assembly, the implantable device including a controller circuit to communicate with a neural stimulator, a telemetry circuit to communicate with the controller circuit and an external module, a memory circuit to communicate with the controller circuit, and computer-readable instructions embedded in the memory circuit, the computer-readable instructions being operable on by the controller to deliver a programmable electric pulse therapy to inhibit heart failure remodeling, where the therapy is delivered from the neural stimulator through the expandable electrode to depolarize the vagus nerve trunk in the cervical region.

25. The system of claim 24, wherein the instructions are further operable on the controller to transvascularly stimulate the vagus nerve trunk to deliver antiarrhythmia therapy following myocardial infarction.

26. The system of claim 24, wherein:
the expandable electrode is configured to abut a predetermined surface area of the internal jugular vein along about 1 centimeter of the IJV, the expandable electrode having an expanded diameter dimensioned and configured to fix the electrode in place in the blood vessel by frictional forces; and
the expandable electrode includes a mesh, at least part of the mesh being conductive.

27. The system of claim 26, wherein the expandable electrode includes a drug-eluting coating that prevents inflammation of stimulated tissue.

28. The system of claim 24, wherein the programmable electric pulse therapy includes an approximately 20 hertz pulse train.

* * * * *

UNITED STATES PATENT AND TRADEMARK OFFICE
CERTIFICATE OF CORRECTION

PATENT NO. : 7,499,748 B2  
APPLICATION NO. : 11/103245  
DATED : March 3, 2009  
INVENTOR(S) : Moffitt et al.

It is certified that error appears in the above-identified patent and that said Letters Patent is hereby corrected as shown below:

In column 7, line 42, in Claim 1, delete "transvasculary" and insert -- transvascularly --, therefor.

In column 8, line 50, in Claim 19, delete "transvasculary" and insert -- transvascularly --, therefor.

In column 9, line 20, in Claim 24, delete "transvasculary" and insert -- transvascularly --, therefor.

Signed and Sealed this

Twenty-sixth Day of May, 2009

JOHN DOLL  
*Acting Director of the United States Patent and Trademark Office*